United States Patent
Schmolz

(10) Patent No.: US 6,410,334 B1
(45) Date of Patent: Jun. 25, 2002

(54) METHOD FOR DETERMINING THE IMMUNE DEFENSE OF BLOOD AND TEST KIT FOR THE SAME AND USE OF A SUITABLE BLOOD SAMPLING SYSTEM

(75) Inventor: Manfred Schmolz, Reutlingen (DE)

(73) Assignee: EDI (Experimentelle & Diagnostische Immunologie) GmbH, Reutlingen (DE)

( * ) Notice: Subject to any disclaimer, the term of this patent is extended or adjusted under 35 U.S.C. 154(b) by 0 days.

(21) Appl. No.: 09/762,189

(22) PCT Filed: Aug. 4, 1999

(86) PCT No.: PCT/EP99/05635

§ 371 (c)(1),
(2), (4) Date: Mar. 16, 2001

(87) PCT Pub. No.: WO00/08464

PCT Pub. Date: Feb. 17, 2000

(30) Foreign Application Priority Data

Aug. 7, 1998 (DE) .......................... 198 35 721

(51) Int. Cl.[7] .......................... G01N 33/48; C12Q 1/00; C12Q 1/02
(52) U.S. Cl. ................. 436/63; 435/4; 435/29
(58) Field of Search ...................... 435/29, 2, 4; 436/63, 436/504

(56) References Cited

U.S. PATENT DOCUMENTS 4,615,341 A * 10/1986 Marzolf et al.
4,745,058 A * 5/1988 Mitsuhashi
5,128,270 A 7/1992 Delacroix et al.
5,334,504 A * 8/1994 Wood et al.

FOREIGN PATENT DOCUMENTS

| DE | 35 42 331 | 6/1987 |
| DE | 41 28 923 | 4/1992 |
| DE | 196 20 443 | 11/1997 |
| EP | 0 031 900 | 7/1981 |
| EP | 0 055 859 | 7/1982 |
| EP | 0 294 216 | 12/1988 |
| EP | 0 296 158 | 12/1988 |
| GB | 2232599 A * | 12/1990 |
| WO | 88/09508 | 12/1988 |
| WO | 90/05541 | 5/1990 |

OTHER PUBLICATIONS

WO 97/29369. De Rooij et al. (1997). Method and kit for separating plasma from whole blood.*
Derwent abstract (Acc. No. 1992–038446) of JP 03285692A, 1991. Human natural tumor necrosis factors preparation.*

* cited by examiner

Primary Examiner—Ralph Gitomer
Assistant Examiner—Mahreen Chaudhry
(74) Attorney, Agent, or Firm—Nath & Associates PLLC; Gary M. Nath; Joshua B. Goldberg

(57) ABSTRACT

The invention relates to a method for the determination of the immune defence activity of blood by the stimulation of white cells in the whole blood, incubation of the whole blood, separation of the supernatant from the sediment and determination of the activity from the separated supernatant. he invention also relates to a test kit for performing the method and to the use of a suitable blood sampling system, particularly a syringe cylinder for this purpose.

18 Claims, 1 Drawing Sheet

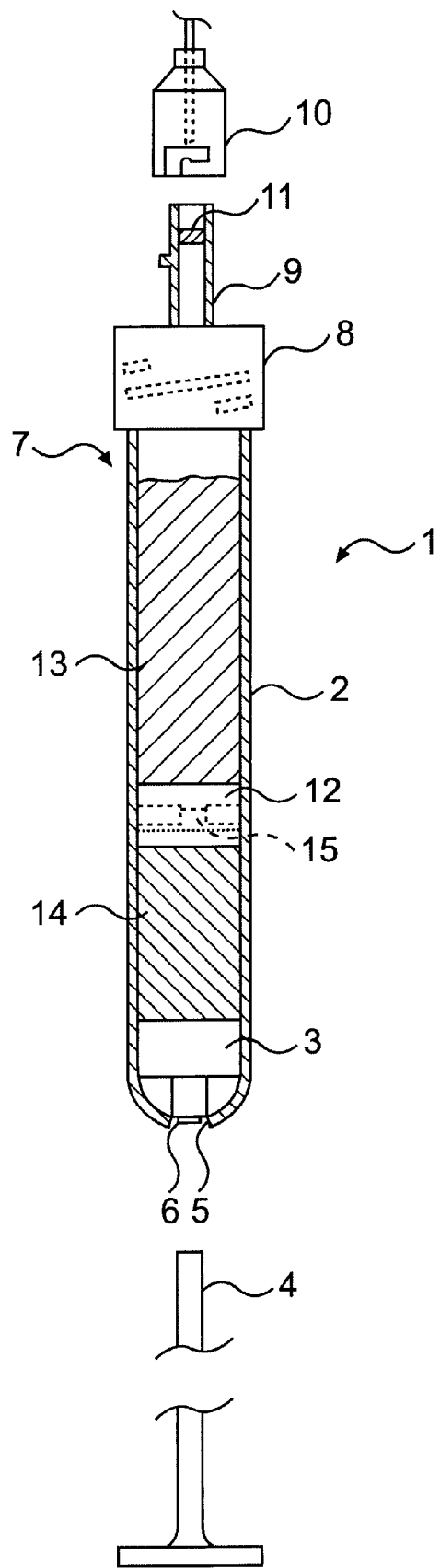

METHOD FOR DETERMINING THE IMMUNE DEFENSE OF BLOOD AND TEST KIT FOR THE SAME AND USE OF A SUITABLE BLOOD SAMPLING SYSTEM

BACKGROUND OF THE INVENTION

1. Field of the Invention

The invention relates to a method for determining the immune defence activity of blood, a test kit for performing the determination and the use of a medical blood sampling system for the determination.

2. Description of the Prior Art

The immune defence activity of blood is determined in order to establish whether blood-conveying organisms, particularly mammals and humans, suffer from a disorder, particularly a weakness of the immune system. In the hitherto known methods blood samples are separated after removal, after which there is a separate treatment and examination of white blood corpuscles. It has been found that as a result of storage and transportation, which can last up to 24 hours and in particular in summer is associated with an undesired thermal effect, a considerable part of the activity of the white blood corpuscles can be lost. Research has revealed that within an hour some cells lose 50% of their activity.

White and red blood cells are separated, because blood red cells are considered responsible for disturbing the activity determination of the white blood cells. Following separation the white blood cells are stored in a buffer medium in the presence of nutrient salts and vitamins. It has been found that an activity change is also possible in such a nutrient solution.

The problem of the invention is therefore to improve the reliability and handling of such activity determinations.

Some blood cells are immediately suitable for testing. However, most cells must be activated in such a way that their metabolism is transposed, i.e. new genes are activated, which generally takes at least 6 to 8 hours. It has now been found that the reliability and reproducibility of activity determination can be significantly improved if an incubation and in particular stimulation of the blood cells is carried out substantially immediately after blood sampling without there being any separation into white and red blood cells. According to the invention the white blood corpuscles are incubated and optionally stimulated for as long as they are in the whole blood. The blood separates itself during incubation without centrifuging being necessary. The supernatant then contains the mesenger substances cytokines) supplied by the white blood cells and which represent a measure for the activity of the cells and which can e.g. be found and determined by ELISA. The expression cytokines, apart from cytokines in the narrower sense, also covers other messenger substances such as e.g. histamine, prostaglandins, leucotrienes, etc.

SUMMARY OF THE INVENTION

Thus, the invention provides a method for determining the immune defence activity of the blood by incubating the blood without prior separation, particularly in conjunction with a stimulation of the white blood cells in the whole blood, separation of the supernatant from the sediment and determination of the activity of the blood cells from the separated supernatant.

In many respects the invention leads to the avoiding of errors.

1. Systematic Errors.

Cells normally react on stimulants, e.g. medicaments, not only in an allergic manner, but also on the combination of the stimulants with proteins (carrier proteins), e.g. albumin or lipoprotein, or in combination with other cells, e.g. antigen-presenting cells (APC). In turn, they have surfaces detectable by receptors. The presence of such costimulating signals is additionally necessary in order to bring about a very precise imaging of the natural activities, also to be expected in vivo, of the cells to be examined. Unlike in the case of cultures with isolated leucocytes, whole blood cultures contain said constituents and signals, so that the reaction of the blood cells, for as long as they are present in the whole blood, corresponds more to the natural conditions than in the isolated state. It has also been found that isolated leucocytes have a much greater reaction on stimulants and medicaments than when contained in whole blood, because in whole blood the stimulants and medicaments are frequently bound to erythrocytes and carrier proteins. As a result of this binding the concentration of the stimulants and medicaments is buffered off, which leads to a more gradual release of the messenger substances delivered by the cells.

2. Elimination of Handling Errors.

As stated above, it has been found that the red blood corpuscles do not disturb the activation of the white blood cells (leucocytes) contrary to what has been standing opinion up to now and instead reflect the conditions such as exist in vivo. However, as a result of the separation of the supernatant following incubation it is possible to ensure in a simple manner that the supernatant is not subsequently influenced by the red blood corpuscles (erythrocytes). This has a favourable effect on the storage or dispatch normally necessary after incubation, in that through the introduction of separation the secretion of cytokines in the supernatant is instantaneously prevented and as a result the cell reactions can be ended at a very clearly defined time.

The invention also makes it possible to establish pharmacological and toxicological effects on the immune system.

In a preferred embodiment, without any prior separation, the whole blood is mixed in extracorporeal manner with a blood clotting agent and preferably at least one stimulant (activating agent) for stimulating blood cells, all the blood is incubated in order to stimulate the blood cells, the supernatant form is separated from the sediment and the immune defence activity is determined from the supernatant. The term blood clotting agent more particularly means an anticoagulant with the aid of which the blood is prevented from clotting or coagulating during and after sampling. Incubation preferably takes place in the presence of a nutrient medium. Preferably the nutrient medium is brought together with the blood clotting agent, particularly anticoagulant and in particular with the at least one stimulant before mixing takes place with the blood. As a result the nutrient medium is mixed with the blood in a volume ratio of 5:1 to 1:5, particularly 1:1 to 1:2. The nutrient medium can be placed beforehand in the vessel in which incubation and/or culturing is performed. To obtain reproducible results it is important that incubation is carried out at a constant temperature, more particularly at approximately 37° C. This can appropriately take place in a heating block, which preferably has several reception openings for incubation vessels. Besides using heating blocks, the invention also covers the use of other thermostatically controllable devices. Thus, incubation can also take place in a water bath or e.g. in a corresponding thermostatically controlled cabinet or the like. The incubation period can be a few minutes to approximately 60 hours and is in particular between 8 and 60 hours. The appropriate incubation period is 24 or 48 hours. This also aids the acquisition of reproducible values. During the incubation period the red and white blood corpuscles normally automatically settle. The separation of the supernatant from the blood corpuscles is consequently advantageously carried out without prior centrifuging. Particularly with short incubation periods, it can also be advantageous to carry out centrifuging for the sedimentation of the solid constituents of the blood. The activity can be determined on the supernatant by determining the messenger substances (cytokines) separated from the blood cells. Determination more particularly takes place in per se known manner by ELISA or other suitable testing methods.

Generally the whole blood is incubated in the presence of at least one stimulant. However, working can also take place without stimulants, e.g. if it is to be established to what extent the cells are already prestimulated in the body.

Generally activity determination takes place at a different location to the incubation, or for other reasons activity determination does not take place directly after the end of incubation. Thus, it is advantageous according to the invention to store in cooled state the supernatant until activity determination takes place, particularly at temperatures of 0 to 8° C., more especially at approximately 4° C. Freezing is also possible in special cases. As the supernatant and also preferably the settled blood corpuscles remain in the incubation vessel after separation, the sediment is cooled with the blood corpuscles. It is particularly preferred for the blood sampling system used for sampling purposes to be used also as an incubation vessel. Preferably a conventional syringe cylinder is used as the blood sampling system. However, the invention also covers other blood sampling systems, such as e.g. evacuated glass tubes with a rubber seal on which can be fitted cannulas. The separation of the supernatant from the blood corpuscles is preferably performed in the blood sampling system, particularly with the aid of a temporarily permeable membrane or partition. For this purpose it is particularly advantageous to have a plunger displaceable in the blood sampling system. The blood sampling system used for blood sampling purposes can also be advantageously used, following the separation of the supernatant and blood corpuscles, as a cooling, transportation and in particular dispatch container. Dispatch can take place in so-called cooling or refrigerating blocks, which are filled with a cold storage medium and preferably have a blind hole serving as an insertion opening for receiving the blood sampling system, particularly the syringe cylinder.

The syringe cylinder for performing the method according to the invention can with particular advantage be in the form of the syringe cylinder with the break-off piston rod and a cap on the side of the needle freeing the entire cylinder cross-section commercially available under the name Monovette (registered trademark of Sarstedt). Such syringe cylinders can be handled in the same way as test tubes or centrifuge tubes after breaking off the piston rod. After the incubation period and the settling of the blood corpuscles, a plunger associated with the syringe cylinder can be inserted from above with the cap removed and pressed into the supernatant, which flows through the plunger and at the end of the pressing-in process and the extraction of a press-in rod closes of its own accord, so that subsequently a mixing of the blood corpuscles and supernatant cannot take place. The blood corpuscles trapped in the lower part of the syringe cylinder and the supernatant separated therefrom and located in the upper part are left in the syringe cylinder during further handling until the supernatant is removed for carrying out the activity determination. Syringe cylinders are commercially available which, for blood sampling purposes, contain an anticoagulant, e.g. heparin, particularly in lyophilized form. Such syringe cylinders usually also contain plastic beads in order to bring about a rapid separation of the red corpuscles from the supernatant. In the case of the method according to the invention the syringe cylinder preferably also contains an anticoagulant, but not the normally present plastic beads. Advantageously, in the method according to the invention, the syringe cylinder also contains at least one stimulator, preferably also in dry, particularly lyophilized form. However, it is also possible to separately store the at least one stimulator, e.g. in the form of a stabilized solution and to place it separately in the syringe cylinder, particularly shortly before blood sampling. Prior to blood sampling the desired nutrient medium volume can be introduced into the sydringe cylinder, particularly by suction from a perforating blood. During blood sampling there is then an immediate mixing with the nutrient medium in which also the previously introduced substances are dissolved.

In a further preferred embodiment of the invention at the time of blood sampling the blood sampling system exclusively contains the blood clotting agent, particularly the anticoagulant. This embodiment avoids the risk of an accidental reinjection of the content of the blood sampling system (e.g. stimulants and/or nutrient medium) into the person, where damage may be caused. After blood sampling, in this embodiment, the further additives, such as e.g. stimulants and/or nutrient medium, are added to the blood in the blood sampling system. This can in particular take place by suction from corresponding perforating bottles.

Stimulants can be used alone or combined with one another. Stimulants which can be used are in particular mitogens, which are substances activating cell division. Numerous different types exist and are inter alia used for activating the different subtypes of lymphocytes. There are also particulate activators of granulocytes and monocytes, such as zymosan and bacteria. Granulocytes and monocytes can also be activated by soluble signal substances such as LPS and muramyl peptides. It is also possible to use antigens and allergens, as well as antibodies against surface structures of the cells, in order to stimulate in preferred manner selectively determined cells.

Th2-lymphocytes have a particularly good combined activating action, i.e. using several stimulators. Mitogen and/or phorbol esters combined with antibodies, e.g. anti-CD 28 are suitable. The latter is a costimulating coactivator. Iio channel-forming ion charging agents are also suitable. If the stimulators release competing mediators, e.g. interleukin 4 and interferon gamma from T-cells, then preferably at least two different batches are used. This is particularly important when examining the blood of allergic and atopic subjects, such as those with neurodermatitis, where too much interleukin 4 is formed. The large number of activity determinations which can be performed is illustrated by this nonexhaustive list. It is consequently possible to keep in stock the blood sampling systems, particularly syringe pistons for blood sampling adapted to the particular determination types and which already can contain the specific stimulants in each case.

The invention consequently also relates to test kits for the determination of the immune defence activity of blood cells and which comprise a) blood sampling instruments with b) a blood sampling system, particularly a syringe cylinder for blood sampling, c) an anticoagulant, which is preferably stored in lyophilized form in the blood sampling system, particularly in the syringe cylinder, d) optionally at least one stimulant for activating the blood cells and which is preferably stored in dried, particularly lyophilized form in the blood sampling system, particularly in the syringe cylinder, or in a separate vessel, e) a culture solution for culturing the sampled blood and f) a plunger fitting into the blood sampling system, particularly the syringe cylinder, for the separation of settled, red blood corpuscles from the supernatant in the blood sampling system.

The culture solution is preferably stored in a perforating bottle, the volume of the latter preferably corresponding to the nutrient solution volume suitable for culturing. Through a complete emptying of the storage bottle before or after blood sampling, the correct volume is transferred into the blood sampling system, particularly into the syringe cylinder. Generally the plunger is located outside the blood sampling system and following the settling of the blood corpuscles and following the end of incubation can be introduced into the blood sampling system, particularly the syringe cylinder.

The equipment preferably also includes an aforementioned, thermostatically regulatable device, particularly a heating block, into which can be inserted the blood sampling systems, particularly syringe cylinders, e.g. 20 such cylinders simultaneously, which makes it possible to simultaneously culture several batches. The equipment also includes a suitable cooling device and an adequate number of cooling blocks for transportation. If desired or if special determinations have to be performed, it is also possible to use empty blood sampling systems or those only containing individual substances and then to add to them the substances desired for the special case, such as e.g. combinations of stimulators.

DESCRIPTION OF THE PRESENT INVENTION

Example

Lyophilized heparin and opsonized zymosan as a possible stimulant are placed in a syringe cylinder, e.g. a Sarstedt Monovette. On the syringe cylinder is mounted the associated needle, after which the entire content of a solution of approximately 3 ml is sucked out of a perforating bottle. The blood clotting agent and stimulant are received in the nutrient medium. From the person whose blood is to be examined is then removed 2 ml of blood, which can place within the framework of multiple examinations. The blood removed is mixed with the culture solution and the substances contained therein. After the removal of the syringe needle the syringe piston remains sealed, because a screw cap provided thereon has a self-sealing perforating membrane. When the syringe piston is drawn downwards, the piston rod is broken off by lateral bending away at a predetermined breaking point, so that the syringe piston is usable in the manner of a test tube with closure. The syringe piston is then placed in a heating block together with other syringe pistons, where similar tests are performed and in the same incubation takes place at a constant 37° C. for 24 hours. During this time the cells are stimulated for the delivery of their messenger substances, which are delivered to the serum. During incubation the blood corpuscles settle on the bottom, so that a substantially clear supernatant is left behind. At the end of the incubation period the syringe cylinders are removed from the heating block and opened by removing the cap. With the aid of a ram a plunger, whose external diameter corresponds to the internal diameter of the syringe cylinder, is introduced into the latter and is slowly pressed by the supernatant to just above the sedimented blood corpuscles in the liquid, the valve in the plunge opening and giving rise to a flow of the supernatant into a separate space formed above the plunger. After removing the ram used for this, there is an automatic closure of the valve in the plunger and the syringe cylinder can be resealed by fitting the screw cap. In this way the blood corpuscles are permanently separated from the supernatant, independently of any vibrations to which the syringe piston is exposed thereafter. After the separation of the blood corpuscles and supernatant, the syringe pistons are cooled to a temperature of approximately +4° C. and inserted in cooling blocks, which are also cooled to this temperature or a temperature below it. The cooling capacity of these cooling blocks is dimensioned in such a way that they maintain their temperature in dispatch bags, e.g. air cushion bags, for a dispatch period of at least 24 hours without any risk of an undesired temperature rise. In the test laboratory, which is generally at a location different from that where blood sampling and incubation took place, the activity determination can be performed e.g. by ELISA, using predetermined supernatant volumes. Parallel tests have revealed that in this procedure precise, reproducible activity values are obtained.

The attached drawing shows a preferred embodiment of a syringe cylinder for performing the method according to the invention.

The syringe cylinder 1 has a hollow cylinder 2 in which is sealingly displaceably located a syringe piston 3 with the aid of a piston rod 4. In the vicinity of the piston rod 4 the hollow cylinder 2 has a taper 5, which serves to guide the piston rod 4. In the vicinity of the piston 3, the piston rod 4 has a predetermined breaking point 6, which when the piston is drawn downwards is located close to the taper 5 and permits an easy breaking off of the piston rod when the piston is guided downwards. The hollow cylinder end 7 directed away from the piston rod 4 is open over its entire cross-section and can be closed with a screw cap 8, which has an attaching connecting piece 9 for a syringe needle 10, which can be locked with a bayonet joint. The attaching connecting piece 9 is provided in its interior with a perforatable rubber seal 11, which is perforated on fitting the needle 10 and is sealed again when the needle is removed. With the syringe cylinder 1 is associated a plunger 12 which, in the unused state, is located outside the syringe cylinder and with which is associated a ram, which is not shown in the drawing. With the aid of the ram the plunger can be introduced into the syringe cylinder with the screw cap 8 removed. This introduction takes place following the end of incubation of the blood contained in the syringe cylinder and which has separated into a supernatant 13 and a sediment 14, which contains the blood corpuscles. For the permanent separation of supernatant 13 and sediment 14 the plunger is pressed in up to the boundary between the supernatant and the sediment, the supernatant flowing through the valve 15 of the plunger until the separating process is ended on reaching the boundary between the supernatant and the sediment. On ending the pressing-in process and the extraction of the ram, the valve 15 closes automatically. By refitting the screw cap 8, the syringe piston can be tightly sealed and can be used as a storage, cooling and transportation container, so that the blood or its separated parts do not have to be transferred between blood sampling and the actual activity determination. Syringe cylinders of the described type are commercially available under the name Monovette and plungers under the name Seraplas in each case from Sarstedt, D-51588 Nymbrecht.

What is claimed is:

1. Method for determining the immune defence activity of blood by incubating the whole blood in the presence of nutrient medium and anticlotting agent in a blood sampling system used for blood sampling purposes, blood incubation taking place substantially immediately following blood sampling at approximately 37° C. and for 8 to 60 hours, without prior separation of the red corpuscles, by bringing the blood into contact in extracorporal manner with blood anticlotting agent which includes anticoagulant heparin, at least one stimulant (activating agent) for stimulating the blood cells to deliver messenger substances, followed by a separation of blood corpuscles from the supernatant without prior centrifuging, and the determination of the immune defence activity using the messenger substances contained in the supernatant, using a medical blood sampling system with a displaceable syringe piston, with a temporarily permeable partition for the incubation of whole blood in the blood sampling system and subsequent separation of supernatant serum from the blood corpuscles with the aid of the partition.

2. Method according to claim 1, wherein incubation takes place in the presence of nutrient medium brought together with at least one anticoagulant and also at least one stimulant prior to adding the blood.

3. Method according to claim 1, wherein incubation takes place in the presence of nutrient medium which is brought into contact with the blood following the mixing of the blood with at least one anticoagulant.

4. Method according to claim 1, wherein at least one stimulant is contacted with the blood following the mixing of the blood with at least one anticoagulant.

5. Method according to claim 1, wherein the whole blood is incubated in a thermostatically controllable device.

6. Method according to claim 5, wherein the thermostatically controllable device is a heating block.

7. Method according to claim 1, wherein the incubated blood is cooled after incubation and separation and kept cooled up to activity determination.

8. Method according to claim 1, wherein the blood sampling system used for blood sampling is a syringe cylinder.

9. Method according to claim 1, wherein the temporarily permeable partition is a sealable plunger.

10. Method according to claim 1, wherein the blood anticlotting agent is placed beforehand in the blood sampling system or in a separate vessel in dry form.

11. Method according to claim 1, wherein the separated supernatant is transported in a cooled state.

12. Method according to claim 11, wherein the separated supernatant is transported in a cooling pack.

13. Method according to claim 1, wherein the blood sampling system used for blood sampling purposes is used as a storage and optionally a dispatch container following the separation of the supernatant and the red blood corpuscles.

14. Test kit for determining the immune defence activity of blood cells with
   a) blood sampling instruments with
   b) a blood sampling system for receiving blood,
   c) an anticoagulant,
   d) at least one stimulant for activating the blood cells for the delivery of messenger substances,
   e) a culture solution for the blood and
   f) a plunger fitting into the blood sampling system for the separation of settled blood corpuscles from the supernatant in the blood sampling system.

15. Kit according to claim 14, wherein the blood sampling system is a syringe cylinder.

16. Kit according to claim 14, wherein at least one member selected from the group consisting of a culture solution and a stimulant is contained in a dry form in the blood sampling system.

17. Kit according to claim 14, wherein at least one member selected from the group consisting of a culture solution and a stimulant is contained in volume-dosed manner in at least one perforating bottle.

18. Kit according to claim 14, wherein the plunger is located outside the blood sampling system and following the settling of the blood corpuscles can be introduced into a blood sampling system having a removable cap.

* * * * *